(12) United States Patent
Griesbach et al.

(10) Patent No.: US 7,863,486 B2
(45) Date of Patent: Jan. 4, 2011

(54) ELECTROCHEMICAL PREPARATION OF STERICALLY HINDERED AMINES

(75) Inventors: Ulrich Griesbach, Mannheim (DE); Siegfried R. Waldvogel, Bonn (DE); Itamar Michael Malkowsky, Hassloch (DE); Joern Kulisch, Bonn (DE)

(73) Assignee: BASF SE, Ludwigshafen (DE)

( * ) Notice: Subject to any disclaimer, the term of this patent is extended or adjusted under 35 U.S.C. 154(b) by 170 days.

(21) Appl. No.: 12/306,616

(22) PCT Filed: Jun. 27, 2007

(86) PCT No.: PCT/EP2007/056390

§ 371 (c)(1), (2), (4) Date: May 5, 2009

(87) PCT Pub. No.: WO2008/003620

PCT Pub. Date: Jan. 10, 2008

(65) Prior Publication Data

US 2009/0253937 A1 Oct. 8, 2009

(30) Foreign Application Priority Data

Jul. 4, 2006 (EP) .................. 06116551

(51) Int. Cl.
C07C 209/30 (2006.01)
C25B 3/04 (2006.01)

(52) U.S. Cl. ...................... 564/448; 205/431

(58) Field of Classification Search ........ None
See application file for complete search history.

(56) References Cited

U.S. PATENT DOCUMENTS 3,843,499 A 10/1974 Giese et al.
2008/0064901 A1 3/2008 Griesbach et al.

FOREIGN PATENT DOCUMENTS

DE 2 208 155 8/1973

WO 2006 005531 1/2006

OTHER PUBLICATIONS

Corey, E. J., Katalytische enantioselektive Diels-Alder-Reaktionen: Methoden, mechanistische Grundlagen, Reaktionswege und Anwendungen, Angew. Chem., vol. 144, pp. 1724-1741, (2002).
Nicolaou, K. C. et al., "Die Diels-Alder-Reaktion in der Totalsynthese", Angew. Chem, vol. 114, pp. 1742-1773, (2002).
Schopohl, Matthias C. et al., "Reversible enantiofaciale Differenzierung eines einzelnen heterocyclischen Substrates durch supramolekulare Rezeptoren", Angew. Chem. vol. 115, pp. 2724-2727, (2003).
Schopohl, Matthias C. et al., "Synthesis and Characterization of Enantiomerically Pure Menthylamines and Their Isocyanates", Synthesis, No. 17, pp. 2689-2694, (2003).

*Primary Examiner*—Brian J Davis
(74) *Attorney, Agent, or Firm*—Oblon, Spivak, McClelland, Maier & Neustadt, L.L.P.

(57) ABSTRACT

The present invention relates to a process for preparing an amine, which comprises the step cathodic reduction of a corresponding oxime derivative of the general formula (I)

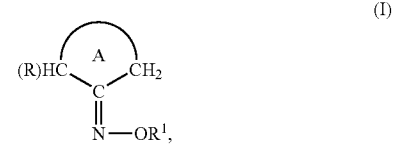

(I)

where
R is $C_{1-6}$-alkyl or $C_{2-6}$-alkenyl which is optionally substituted by one or more substituents selected independently from the group consisting of phenyl, O—$C_{1-6}$-alkyl, NH—$C_{1-6}$-alkyl, N($C_{1-6}$-alkyl)$_2$, OH and NH$_2$;
$R^1$ is H; $C_{1-6}$-alkyl or C(O)—$C_{1-6}$-alkyl and
A is a 5-, 6- or 7-membered hydrocarbon ring which is saturated or has a double bond and in which at least one CH$_2$ group may, if appropriate, be replaced by —O—, —S— —NH—, —N= or —N($C_{1-6}$-alkyl)- and which may optionally be substituted by one or more further substituents selected independently from the group consisting of phenyl, $C_{1-6}$-alkyl, O—$C_{1-6}$-alkyl, NH—$C_{1-6}$-alkyl, N($C_{1-6}$-alkyl)$_2$, OH and NH$_2$;
wherein, based on the ring carbon bearing the substituent R, the oxime derivative has an excess of the R or S form of at least 10%.

10 Claims, No Drawings

ELECTROCHEMICAL PREPARATION OF STERICALLY HINDERED AMINES

CROSS-REFERENCE TO RELATED APPLICATIONS

The present application is a 35 U.S.C. § 371 National Stage patent application of International patent application PCT/E07/56390, filed on Jun. 27, 2007, which claims priority to German patent application 06116551.0, filed on Jul. 4, 2006.

BACKGROUND OF THE INVENTION

1. Field of the Invention

The present invention relates to a process for preparing an amine by cathodic reduction of a corresponding oxime derivative.

2. Description of the Background

Organic compounds having a plurality of chiral centers are frequently important building blocks and auxiliaries in the synthesis of other organic compounds in order to introduce the chiral centers mentioned or in order to build up a nonracemic stereocenter. Here, compounds which have a comparatively rigid skeleton and additionally comprise voluminous groups which can exercise a directing action in the synthesis of other organic compounds are frequently chosen as auxiliaries.

Cyclic compounds from the "chiral pool" are frequently of interest here. Particular mention may be made of cyclic terpenoids.

An example of such a compound is 8-phenylmenthol which is used, for example, as auxiliary in the asymmetric Diels-Alder reaction (E. Corey, Angew. Chem. 114 (2002), 1724-1741; K. C. Nicolaou, Angew. Chem. 114 (2002), 1742-1773).

Here, the hydroxyl group of menthol serves as functional group to introduce the auxiliary into a molecule so that a prochiral center is converted into a chiral center in a subsequent chemical reaction under the directing action of the auxiliary. However, menthol which can be used, for example, as alcohol component of an ester is comparatively labile and is therefore not the agent of choice for every reaction.

There is therefore a need to provide an amine analogue of menthol, derivatives thereof or analogous chiral auxiliaries.

The amine analogue of menthol and 8-methylmenthol has been used, for example, by M. C. Schopohl et al., Angew. Chem. 115 (2003), 2724-2727, in order to study the enantiofacial differentiation of individual caffeine gas molecules.

To obtain amine analogues of menthol, M. C. Schopohl et al., Synthesis 17 (2003), 2689-2694, propose preparing the corresponding amine from (+)-pulegone. As first step of the synthesis, the ethylenic double bond is reacted with a Grignard reagent to introduce a radical in the 8 position. This makes derivatization in said 8 position possible. The reaction produces a chiral center on the ring carbon in the 4 position. The Grignard reaction is unable to distinguish between the R and S form, resulting in formation of an epimer mixture in the reaction. After conversion of the keto function into an oxime, the (4S) epimer can be obtained. In the subsequent Beauvault-Blanc reaction with sodium in toluene, the oxime function is converted into an amino function which is present in the transconfiguration relative to the alkyl radical in the 4 position.

This represents a critical step in the synthesis in order to obtain a configuration corresponding to that of menthol.

In contrast to the above-described reduction with sodium, in the heterogeneous reduction over transition metal catalysts, either no reaction takes place or the corresponding amine is accompanied by an equimolar amount of an epimeric amine which can be separated off only with difficulty.

However, a disadvantage of the above-described reaction is the use of sodium, which, in addition, is used in comparatively large amounts.

SUMMARY OF THE INVENTION

It is therefore an object of the present invention to provide an alternative process for preparing an amine with the aid of a corresponding oxime derivative which makes discrimination of the R or S form at a ring carbon which bears the oxime function or a derivative thereof and which has a substituent in the α position possible.

This object is achieved by a process for preparing an amine, which comprises the step cathodic reduction of a corresponding oxime derivative of the general formula (I)

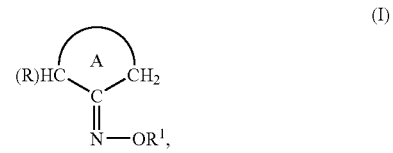

where
R is $C_{1-6}$-alkyl or $C_{2-6}$-alkenyl which is optionally substituted by one or more substituents selected independently from the group consisting of phenyl, O—$C_{1-6}$-alkyl, NH—$C_{1-6}$-alkyl, N($C_{1-6}$-alkyl)$_2$, OH and NH$_2$;
$R^1$ is H; $C_{1-6}$-alkyl or C(O)—$C_{1-6}$-alkyl and
A is a 5-, 6- or 7-membered hydrocarbon ring which is saturated or has a double bond and in which at least one CH$_2$ group may, if appropriate, be replaced by —O—, —S— —NH—, —N= or —N($C_{1-6}$-alkyl)- and which may optionally be substituted by one or more further substituents selected independently from the group consisting of phenyl, $C_{1-6}$-alkyl, O—$C_{1-6}$-alkyl, NH—$C_{1-6}$-alkyl, N($C_{1-6}$-alkyl)$_2$, OH and NH$_2$;

wherein, based on the ring carbon bearing the substituent R, the oxime derivative has an excess of the R or S form of at least 10%.

DESCRIPTION OF THE INVENTION

It has surprisingly been found that cathodic reduction of a corresponding oxime derivative allows the desired, above-described discrimination and thus makes an electrochemical preparation of corresponding amines in which a radical R which is in the trans position relative to the amine function is located in the α position possible without, for example, elemental sodium having to be used.

In the oxime derivative of the general formula (I), the radical R which is located in the α position relative to the future amine function is a $C_{1-6}$-alkyl or $C_{2-6}$-alkenyl radical which is unsubstituted or has one or more substituents. Possibilities for the substituent or substituents are phenyl, O—$C_{1-6}$-alkyl, NH—$C_{1-6}$-alkyl, N($C_{1-6}$-alkyl)$_2$, OH and NH$_2$. If a plurality of substituents are present, these can be selected independently from the abovementioned group.

The radical R is preferably a $C_{1-6}$-alkyl or $C_{2-6}$-alkenyl radical which is unsubstituted or has not more than one substituent.

For the purposes of the present invention, the term "$C_{1-6}$-alkyl" refers to an alkyl radical which has from 1 to 6 carbon atoms and is unbranched or branched. Examples of such substituents are methyl, ethyl, n-propyl, isopropyl, n-1-butyl, n-2-butyl, sec-butyl, tert-butyl, n-1-pentyl, n-2-pentyl, n-3-pentyl, n-hexyl.

Furthermore, for the purposes of the present invention, the term "$C_{2-6}$-alkenyl" refers to an alkenyl radical which has from 2 to 6 carbon atoms and is unbranched or branched. Examples are vinyl, allyl, n-1-propenyl, n-2-propenyl, butenyl, pentenyl, hexenyl.

The radical R is preferably an unsubstituted $C_{1-6}$-alkyl radical, an unsubstituted $C_{2-6}$-alkenyl radical or a phenyl-substituted $C_{1-6}$-alkyl radical.

R is very particularly preferably isopropyl, tert-butyl or 1-phenyl-1-methylethyl.

The oxime derivative of the general formula (I) can be an oxime as such. Furthermore, the hydrogen of the oxime group may be replaced by a $C_{1-6}$-alkyl or C(O)—$C_{1-6}$-alkyl radical. The oxime derivative is preferably an oxime ($R^1$=H) or $R^1$ is methyl or acetyl. The oxime derivative is very particularly preferably an oxime.

Furthermore, the oxime derivative of the general formula (I) has a ring A. This comprises the carbon which bears the oxime or an analogue of oxime and also the carbons directly adjacent to this carbon. All together, the ring A has 5, 6 or 7 ring atoms. The ring A is a hydrocarbon ring which is saturated or has a double bond. The ring A can be a cyclopentane, cyclopentene, cyclohexane, cyclohexene, cycloheptane or cycloheptene ring.

Furthermore, a $CH_2$ group of the ring A may be replaced by —O—, —S—, —NH— or —N($C_{1-6}$-alkyl). It is likewise possible for a plurality of $CH_2$ groups to be replaced by one of the abovementioned heteroatoms. If a plurality of heteroatoms are present as ring atoms in ring A, these can be selected independently of one another. When a double bond is present in ring A and at least one $CH_2$ group has been replaced by a heteroatom and this at least one heteroatom is nitrogen, the latter can occur as imino nitrogen. It is also possible for a plurality of these nitrogens to be present.

The ring A can have no substituent, one substituent or a plurality of substituents in addition to the radical R and the oxime group or its analogue. The substituent or substituents can be selected from the group consisting of phenyl, —$C_{1-6}$-alkyl, O—$C_{1-6}$-alkyl, NH—$C_{1-6}$-alkyl, N($C_{1-6}$-alkyl)$_2$, OH and $NH_2$. If a plurality of substituents are present, these can be selected independently from the abovementioned group. The substituent is preferably a $C_{1-6}$-alkyl group. Particular preference is given to methyl.

The ring A preferably has precisely one further substituent.

Of course, the ring A of the oxime derivative of the general formula (I) in each case has the radical R and the oxime or the oxime analogue as substituent.

If the ring A is not made up exclusively of carbon atoms, the ring can be, for example, a tetrahydrofuran, dihydrothiophene, dihydrofuran, dihydropyrrole, oxane, thiane, piperidine, dihydropyran or tetrahydropyridine. However, the ring A preferably has no heteroatoms. The ring A is very particularly preferably cyclohexane or cyclohexene, in particular cyclohexane.

The oxime derivative of the general formula (I) is very particularly preferably a methyl-substituted oxime derivative selected from the group consisting of

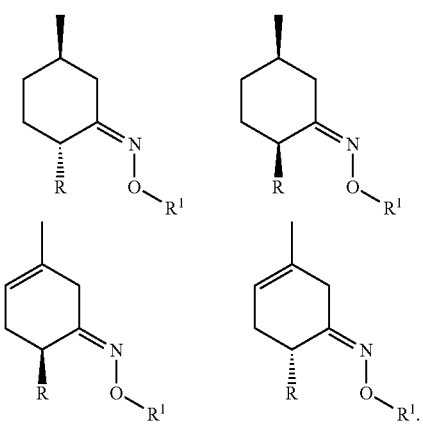

Very particular preference is given to oxime derivatives of the general formula (I) which after reduction give menthylamine, 8-methylmenthylamine or 8-phenylmenthylamine.

Here, the radicals R, $R^1$ are as defined above.

The oxime derivatives for the process of the invention can be obtained by preparative methods known in the prior art. A typical precursor here is the corresponding ketone.

One possible method of preparation is to start out from the corresponding aromatic system which bears the desired substituents in order to build up the desired oxime derivative after reduction and separation of diastereomers. If a double bond is present in the ring A, this could be obtained by stepwise reduction or by means of a reduction/elimination reaction. Separations are described, for example, by H. Feltkamp et al., Liebigs Ann. Chem. 707 (1967), 78-86.

The synthesis of the oxime is preferably carried out using the "chiral pool". Such a strategy is described, for example, by M. C. Schopohl et al., Synthesis 17 (2003), 2689-2694. A preferred starting material is pulegone or menthone.

The objective of the present invention is to provide a process for the cathodic reduction of an oxime derivative to form a corresponding amine in which the oxime function or the oxime analogue bears a radical R in the α position, with the amino function being located predominantly in the transposition relative to the radical R after reduction. However, a prerequisite for this is that the chiral ring carbon which bears the radical R is not present in racemic form.

An excess of the R or S form of at least 10%, preferably at least 50%, more preferably at least 75%, even more preferably at least 90%, even more preferably at least 95%, even more preferably at least 98%, even more preferably at least 99%, in particular at least 99.9%, should therefore be present in the oxime derivative of the general formula (I) for the purposes of the present invention. The ring carbon which bears the substituent R is very particularly preferably present exclusively in the R or S form.

If further stereocenters are present in the oxime derivative, what has been said above applies analogously to these.

The excess of the R or S form is given by the formula $$E\;[\%] = \frac{|n_R - n_S|}{n_R + n_S} \cdot 100,$$

where E is the excess in % and n is in each case the molar amount of the R or S form based on the ring carbon which bears the substituent R.

If the ring carbon which bears the substituent R is the only stereocenter in the oxime derivative of the general formula (I), the above-defined excess is the enantiomeric excess of the oxime derivative.

If at least one further stereocenter is present, the excess is an epimeric excess based on the ring carbon which bears the substituent R.

The determination of the above parameters for determining the excess can be carried out by means of methods known in the prior art. If the excess is an enantiomeric excess, a corresponding evaluation can be effected by customary methods, for example circular dichroism. A further method of determination would be to prepare a derivative of the oxime derivative of the general formula (I) so that the product obtained is present as diastereomer and the customary methods for diastereomers can be employed. One of the most-used methods is nuclear resonance spectroscopy.

After reduction of the oxime to the amine, a further chiral carbon atom is present, with a discrimination between R and S forms occurring due to the electrochemical reduction, so that an excess based on this carbon atom which is greater than 0% is achieved. The excess is preferably at least 10%, more preferably at least 50%, in particular at least 60%.

The electrochemical reduction of oximes at a cathode is known from WO-A 2006/005531.

The reduction can, for example, be carried out in a divided or undivided flow cell. Preference is given to using a divided flow cell.

The catholyte may comprise a solvent in addition to the amine formed during the reaction and the oxime derivative. The solvent is one of the inert solvents generally customary in organic chemistry, e.g. dimethyl carbonate, propylene carbonate, tetrahydrofuran, dimethoxyethane, acetonitrile or dimethylformamide. A $C_1$-$C_4$-alkyl alcohol is preferably used as solvent. $C_5$-$C_7$-hydrocarbons such as hexane are also suitable as solvents in combination with the abovementioned solvents. Cyclic or acyclic ethers can likewise be used. It is likewise possible to use water. In addition, it is possible to use mixtures of the abovementioned solvents.

Preference is given to alcohols, water, ethers or mixtures thereof. A single-phase or multiphase system can be formed.

Very particular preference is given to alcohols, which may, if appropriate, be present in mixtures with one another and/or water, and $C_{1-4}$-alkanols such as methanol, ethanol, n-propanol, i-propanol, n-butanol, sec-butanol, tert-butanol; diols such as glycol, triols such as glycerol, polyols, polyethers or alkoxyalkanols such as ethylene glycol monomethyl ether or dimethoxyethane. Very particular preference is given to dimethoxyethane.

To establish conductivity, the catholyte generally comprises a mineral acid, preferably sulfuric acid or an alkali metal ($C_1$-$C_4$)-alkyl alkoxide, preferably sodium methoxide.

In general, an electrolyte salt is added to the anolyte and, if appropriate, also to the catholyte (in addition to one of the abovementioned agents which establish conductivity). Alkali metal salts or tetra($C_1$-$C_6$-alkyl)ammonium salts, preferably tri($C_1$-$C_6$-alkyl)methylammonium salts, are generally used for this purpose. Possible counterions are sulfate, hydrogensulfate, alkylsulfates, arylsulfates, halides, phosphates, carbonates, alkylphosphates, alkylcarbonates, nitrate, alkoxides, tetrafluoroborate, hexafluorophosphate or perchlorate.

Preference is given to methyltributylammonium methylsulfate (MTBS), methyltriethyl-ammonium methylsulfate or methyltripropylammonium methylsulfates.

The anolyte preferably likewise comprises a solvent comprising water, an alcohol or a plurality of alcohols or a mixture of two or more of the solvents. For the anolyte, it is in principle possible to use the same alcohols as for the catholyte, but these can also be different from the catholyte.

The process of the invention can preferably be carried out in all customary divided types of electrolysis cell in order to be able to exclude the possibility of substances such as products undergoing secondary chemical reactions due to the cathode process in the process of the invention. The process is preferably carried out continuously in divided flow cells.

Divided cells having a parallel electrode arrangement are preferably used. As dividing media, it is possible to use ion-exchange membranes, microporous membranes, diaphragms, filter fabrics made of materials which do not conduct electrons, glass frits and porous ceramics. Preference is given to using ion-exchange membranes, in particular cation-exchange membranes. These conductive membranes are commercially available, e.g. under the trade name Nafion® (from E.T. DuPont de Nemours and Company) and Gore Select® (from W. L. Gore & Associates, Inc.).

Cathodes used are preferably ones whose cathode surface is formed by a material having a high hydrogen overvoltage, e.g. lead, zinc, tin, nickel, mercury, cadmium, copper or alloys of these metals or glassy carbon, graphite or diamond.

Particular preference is given to diamond electrodes as described, for example, in EP-A-1036863.

Possible anodes are in principle all customary materials, preferably those also mentioned as cathode materials. In the case of an acidic anolyte, preference is given to using platinum, diamond, glassy carbon or graphite anodes or the dimensionally stable anodes (DSA) known to those skilled in the art. If the anolyte is basic, preference is given to using stainless steel.

The anode reaction can be chosen freely, but preference is given to oxidation of the solvent, for example a $C_1$-$C_4$-alcohol. When methanol is used, methyl formate, formaldehyde dimethyl acetal or dimethyl carbonate is formed. A sulfuric acid solution diluted with a $C_1$-$C_4$-alcohol, for example, is used for this purpose.

The current densities at which the process is carried out are generally from 1 to 1000 mA/cm², preferably from 10 to 100 mA/cm². The process is generally carried out at atmospheric pressure. Higher pressures are preferably employed when the process is to be carried out at relatively high temperatures in order to avoid boiling of the starting compounds or solvents.

After the reaction is complete, the electrolyte solution is worked up by general separation methods. For this purpose, the catholyte is generally firstly distilled and the individual compounds are obtained separately in the form of different fractions. Further purification can be effected, for example, by crystallization, distillation or chromatography.

EXAMPLES

Example 1

Electrochemical Reduction of (−)-Menthone Oxime

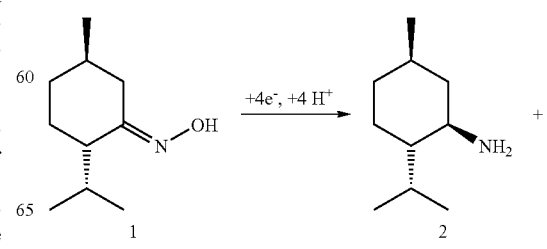

[Structure 3: cyclohexane with NH₂ (wedge), methyl (wedge up), isopropyl (wedge down)]

In a divided electrolysis cell, anolyte and catholyte are reacted electrochemically according to the variants indicated below at a current density of 67 mA/cm², with 8 F/mol being introduced (corresponds to 2 equivalents). The electrolysis is carried out at room temperature; the divided cell is constructed from two flange cells, with anode space and cathode space being separated by a Nafion 324 membrane. The anode material is platinum, and lead is used as cathode.

For the work-up, the reaction mixture is diluted with water (50 ml), brought to pH=1 by means of concentrated sulfuric acid and washed with cyclohexane (4×30 ml). The aqueous phase is subsequently brought to pH=12 by means of 50% strength potassium hydroxide solution and extracted again with TBME (4×50 ml). The combined organic basic extracts are washed with 10% strength sodium hydroxide solution (2×100 ml) and dried over calcium oxide and freed of the solvent on a rotary evaporator. Further purification can be effected, for example, by column chromatography or distillation.

Variant A: Selective for 2
Anolyte: 20 ml of 1 M H₂SO₄
  20 ml of methanol
Catholyte: 2.05 g of (−)-menthone oxime (1) (12.1 mmol)
  20 ml of 1 M H₂SO₄
  20 ml of DME
Cathode material: Mercury
Current density: 23.3 mA/cm²
Temperature: −14–−18° C.
Q/n: 6.6 F/mol of 1 (corresponds to 1.65 equivalents)
Yield: 56% (1.06 g, 6.8 mmol); 2:3=4:1 (epimer ratio determined from chromatographic analyses of the products converted quantitatively into acetamides (epimeric excess de=60%)

Variant B: Selective for 3
Anolyte: 50 ml of 1 M H₂SO₄
  50 ml of methanol
Catholyte: 2.26 g of (−)-menthone oxime (1) (13 mmol)
  25 ml of 1 M H₂SO₄
  75 ml of ethylene glycol monomethyl ether
Cathode material: Lead
Current density: 50 mA/cm²
Q/n: 6 F/mol of 1 (corresponds to 1.5 equivalents)
Yield: 13% (0.93 g, 6 mmol); 2:3=1:0.57 (epimer ratio determined from chromatographic analyses of the products converted quantitatively into acetamides)

Variant C: Epimer mixture
Anolyte: 40 ml of 1 M H₂SO₄
Catholyte: 3.26 g of (−)-menthone oxime (1) (21.7 mmol)
  20 ml of 1 M H₂SO₄
  20 ml of 1,4-dioxane
Cathode material: Lead Yield: 50% (1.69 g, 10.9 mmol); 2:3=5:4 (epimer ratio determined by NMR) (de=11%)

Example 2

Electrochemical reduction of (−)-trans-(1R,4S)-8-phenylmenthyl oxime

Use of electrolyte salts as additive

Anolyte: 50 ml of 0.162M H₂SO₄ in methanol (corresponds to 2% by weight)
Catholyte: 0.51 g of (−)-trans-(1R,4S)-8-phenylmenthyl oxime (0.002 mol) 50 ml of 0.162M H₂SO₄, 0.017M triethylmethylammonium methylsulfate in methanol (corresponds to 2% by weight, 0.5% by weight)
Cathode material: Lead
Current density: 12.5 mA/cm²
Q/n: 10 F/mol of (−)-trans-(1R,4S)-8-phenylmenthyl oxime (corresponds to 2.5 equivalents)
Temperature: 20-22° C.
Yield: 94% (0.45 g, 0.002 mol); diastereomer ratio of (−)-(1R,3R,4S)-8-phenylmenthylamine: (+)-(1R,3R,4R)-8-phenylmenthylamine=6.5:1 (determined by ¹H-NMR spectroscopy), de=73%
Electrolysis apparatus: Divided electrolysis cell
Separation medium: Nafion®
Procedure:

The (−)-trans-(1R,4S)-8-phenylmenthyl oxime is dissolved in the Catholyte and transferred into the cathode half cell. The anode half cell is charged with the anolyte. The electrolysis is carried out galvanostatically at a current density of 12.5 mA/cm² and a temperature of 20-22° C. Platinum serves as anode and lead serves as cathode. After transfer of an amount of charge of 1966 C (10 F/mol of (−)-trans-(1R,4S)-8-phenylmenthyl oxime, 2.5 equivalents), the electrolysis is stopped.

Work-up:

The reaction mixture is transferred from the cathode half cell to a flask and the cell is rinsed with a total of 50 ml of methanol and 50 ml of water. The total reaction mixture and washings from the cathode half cell is set to pH=1 by means of concentrated sulfuric acid and freed of methanol under reduced pressure. The residue is washed with cyclohexane (4×30 ml) and the pH of the aqueous phase is subsequently set to 12 by means of 50% strength potassium hydroxide solution. The mixture is extracted with TBME (4×50 ml), the combined organic phase is dried over calcium oxide and freed of solvent on a rotary evaporator. The (1R,3R)-8-phenylmenthylamine is obtained as a light-yellow liquid.

Observations:

The clamping voltage during the electrolysis is high (up to 20.6 V). After some time, a deposit is formed on the cathode. While only a little gas evolution at the cathode is observed at the beginning, this increases with increasing deposit formation.

Analytical data:
(−)-(1R,3R,4S)-8-phenylmenthylamine

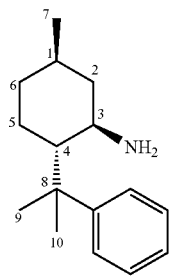

$t_R^A$=20.20 min
$^1$H-NMR (400 MHz; CDCl$_3$) δ (ppm)=0.75 (m, 1H, 2-H$^a$); 0.87 (d, 3H, 7-H, $^3J_{7,1}$=6.5 Hz); 0.91-0.95 (m, 1H, 5-H$_a$); 1.06-1.16 (m, 1H, 6-H$_a$); 1.22 (s, 3H, 10-H); 1.38 (s, 3H, 9-H); 1.40-1.41 (m, 1H, 1-H$_a$); 1.62-1.73 (m, 3H, 2-H$_e$, 4-H$_a$, 6-H$_e$); 1.79-1.85 (m, 1H, 5-H$_e$); 2.60-2.66 (m, 1H, 3-H$_a$); 7.13-7.17, 7.28-7.32, 7.37-7.40 (m, 5H, Ar—H). $^{13}$C-NMR (100 MHz; CDCl$_3$) δ (ppm)=22.2 (C-7); 22.7 (C-9); 27.0 (C-5); 30.6 (C-10); 32.0 (C-1); 35.3 (C-6); 39.9 (C-8); 46.7 (C-2); 53.2 (C-3); 54.2 (C-4); 125.3 (CH—Ar); 128.3 (2×CH—Ar); 152.9 (C$_q$—Ar).

$^A$: Instrument: GC2010 from Shimadzu, Japan.
Column: Fused silica capillary column HP-5 from Agilent, USA (length: 30 m; internal diameter: 0.25 mm; film thickness of the covalently bound stationary phase: 0.25 μm; carrier gas: hydrogen; injector temperature: 250° C.; detector temperature: 300° C.; column admission pressure: 106 kPa).
Program: 50°(10°-80)(2°-100)(15°-270)5'.

The invention claimed is:
1. A process for preparing an amine, which comprises:
cathodically reducing in an electrochemical cell an oxime derivative of formula (I)

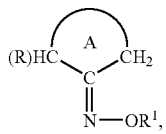

(I)

where
R is an unsubstituted or substituted C$_{1-6}$-alkyl or an unsubstituted or substituted C$_{2-6}$-alkenyl, wherein said substituted C$_{1-6}$-alkyl and said substituted C$_{2-6}$-alkenyl are substituted by at least one substituent selected independently from the group consisting of phenyl, O—C$_{1-6}$-alkyl, NH—C$_{1-6}$-alkyl, N(C$_{1-6}$-alkyl)$_2$, OH and NH$_2$;
R$^1$ is H; C$_{1-6}$-alkyl or C(O)—C$_{1-6}$-alkyl; and
A is a substituted or unsubstituted 5-, 6- or 7-membered hydrocarbon ring which is saturated or has a double bond and in which at least one CH$_2$ group is optionally replaced by —O—, —S— —NH—, —N= or —N(C$_{1-6}$-alkyl)-, wherein said substituted 5-, 6- or 7-membered hydrocarbon ring is substituted by at least one substituent selected independently from the group consisting of phenyl, C$_{1-6}$-alkyl, O—C$_{1-6}$-alkyl, NH—C$_{1-6}$-alkyl, N(C$_{1-6}$-alkyl)$_2$, OH and NH$_2$;
wherein, based on the ring carbon bearing the substituent R, the oxime derivative has an excess of the R or S form of at least 10%.

2. The process according to claim 1, wherein R is isopropyl, tert-butyl or 2-phenyl-2-propyl.

3. The process according to claim 1, wherein R$^1$ is hydrogen.

4. The process according to claim 1, wherein A is a substituted or unsubstituted cyclohexane or a substituted or unsubstituted cyclohexene, wherein said substituted cyclohexane and said substituted cyclohexene are substituted by at least one methyl group.

5. The process according to claim 1, wherein, based on the ring carbon bearing the substituent R, the oxime derivative has an epimeric excess of at least 98%.

6. The process according to claim 1, wherein the oxime derivative is selected from the group consisting of

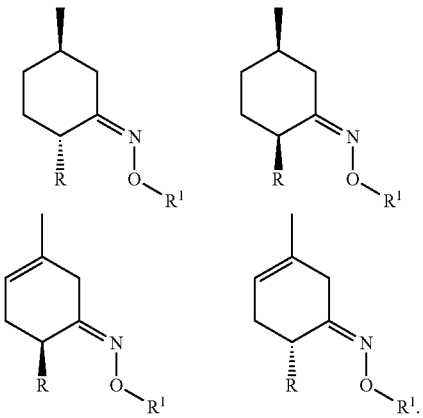

7. The process according to claim 1, wherein the product obtained is menthylamine, 8-methylmenthylamine or 8-phenylmenthylamine.

8. The process according to claim 1, wherein reduction of the oxime derivative is conducted in a divided flow electrochemical cell.

9. The process according to claim 1, wherein the catholyte of the electrochemical cell comprises water, at least one alcohol or ether or mixtures thereof.

10. The process according to claim 1, wherein the anolyte of the electrochemical cell comprises water, at least one alcohol or a mixture thereof.

* * * * *